US005163422A

United States Patent [19]

Burgess

[11] Patent Number: 5,163,422

[45] **Date of Patent: * Nov. 17, 1992**

[54] BREATHING APPARATUS FOR PROVIDING A SOURCE OF BREATHABLE AIR IN A BURNING STRUCTURE

[76] Inventor: Paul D. Burgess, 1085 NW. 3rd Ave., Boca Raton, Fla. 33432

[ * ] Notice: The portion of the term of this patent subsequent to May 5, 2009 has been disclaimed.

[21] Appl. No.: 769,186

[22] Filed: Sep. 30, 1991

Related U.S. Application Data

[63] Continuation-in-part of Ser. No. 679,741, Apr. 3, 1991, Pat. No. 5,109,836.

[51] Int. Cl.[5] ...................... A62B 18/02; A62B 17/04; A62B 23/02; A61M 15/00

[52] U.S. Cl. .......................... 128/200.24; 128/201.24; 128/201.25; 128/205.25

[58] Field of Search ...................... 128/200.24, 201.25, 128/201.26, 204.18, 204.26, 205.12, 205.21, 205.25, 206.12, 201.24

[56] References Cited

U.S. PATENT DOCUMENTS

| | | | |
|---|---|---|---|
| 807,597 | 12/1905 | Carpenter . | |
| 1,040,311 | 10/1912 | Halloran . | |
| 4,320,756 | 3/1982 | Holmes | 128/200.24 |
| 4,331,139 | 5/1982 | Popa | 128/206.12 |
| 4,373,522 | 2/1983 | Zien | 128/200.24 |
| 4,467,796 | 8/1984 | Beagley | 128/205.25 |
| 4,608,975 | 9/1986 | Tannatta | 128/206.12 |
| 4,640,278 | 2/1987 | Barry | 128/206.12 |
| 4,774,939 | 10/1988 | Disney | 128/205.27 |
| 4,901,715 | 2/1990 | Mulcahy | 128/200.24 |
| 4,905,684 | 3/1990 | Heffer | 128/206.28 |
| 4,974,584 | 12/1990 | Goodnoe . | |

FOREIGN PATENT DOCUMENTS

| | | | |
|---|---|---|---|
| 2214820 | 9/1989 | United Kingdom | 128/205.25 |

*Primary Examiner*—Edgar S. Burr
*Assistant Examiner*—Kimberly L. Asher
*Attorney, Agent, or Firm*—Quarles & Brady

[57] ABSTRACT

A breathing apparatus for providing a source of breathable air in a burning structure for the firefighters or occupants trapped in the burning structure includes a hollow body member connected to a hollow piercing means for penetrating a wall of the structure. The piercing means provides orifices for receiving breathable air from an interior cavity of the wall. The breathing apparatus can be equipped with a one-way valve for permitting the transfer of air from the wall cavity to the user but prohibiting the back flow of smoke or other contaminated air through the apparatus to the clean air disposed in the wall cavity. The apparatus can also be equipped with a locking thread for securely engaging the apparatus with the pierced wall and providing sealing engagement of an annular sealing ring with the wall.

7 Claims, 10 Drawing Sheets

BREATHING APPARATUS FOR PROVIDING A SOURCE OF BREATHABLE AIR IN A BURNING STRUCTURE

CROSS-REFERENCE TO RELATED APPLICATION

This application is a continuation in part of U.S. patent application, Ser. No. 679,741, filed Apr. 3, 1991, now U.S. Pat. No. 5,109,836.

FIELD OF THE INVENTION

This invention relates to the field of safety devices and more particularly to an apparatus for providing a source of breathable air in a burning building or the like.

BACKGROUND OF THE INVENTION

It is well known that firefighters and occupants of burning buildings encounter life-threatening situations when smoke and fire in the burning building render available air unsuitable to breath. Many techniques have been developed in the past to provide breathable air to firefighters and occupants in this environment. One well known technique is to provide firefighters with masks coupled to tanks of compressed air. This technique has the disadvantage that the air supply is limited. In one device, disclosed in U.S. Pat. No. 4,974,584, a water hose is provided with an air collar, wherein in an emergency situation, air may be forced through the water hose to provide air to a firefighter or stranded occupant in distress. This system has the disadvantage that it is bulky, and using a water hose to provide a source of air to a firefighter or trapped occupant necessarily removes the water hose from service for its intended purpose. In another system disclosed in U.S. Pat. No. 4,320,756, a breathing apparatus is disclosed wherein a breathing tube is inserted in the water trap of a toilet to expose one end of the breathing tube to air from a vent pipe connected to the sewer line connected to a toilet. While this technique may be effective, it provides a source of air which is less than desirable.

From the foregoing, no technique or apparatus is known which is compact and portable, and which readily provides a source of breathable air to a firefighter or occupant trapped in a burning building at any location in the building.

SUMMARY AND OBJECTS OF THE INVENTION

In summary, the present invention comprises an apparatus for providing breathable air to firefighters and occupants trapped in a burning building. The apparatus can be adapted for use with a conventional face mask and air supply line used by a firefighter. The present invention includes a hollow body member having inlet and outlet ports wherein the outlet port can be adapted for receiving an air line of an air supply type face mask. A peen member can also be formed integrally on one end of the hollow body member. A hollow cylindrical piercing means can be disposed in threadable engagement with the inlet port of the hollow body, wherein the hollow cylindrical piercing means includes a plurality of orifices disposed axially therein. The orifices are adapted for conducting air from the exterior of the piercing means into the hollow body, thus providing a source of air to the outlet of the hollow body member.

The piercing means can be inserted through wall structure to access breathable air disposed in the wall cavity.

A one-way valve can be disposed in the hollow body adjacent to outlet so that breathable air communicated from the wall cavity can be drawn from the hollow body while smoke and exhaled air are restricted from flowing back through the hollow body to the wall cavity air source. The piercing means can also provide a locking thread to lockingly engage the piercing means with the wall in lieu of hand pressure to further reduce the possibility of contamination of the internal wall air source while giving the user free use of his hands.

It is an object of the present invention to provide an apparatus for providing a source of breathable air to firefighters and occupants trapped in a burning building.

It is another object of the present invention to provide a breathing apparatus which is compact and lightweight.

It is still another object of the present invention to provide a breathing apparatus which includes an integral means for creating an opening in a wall from which breathable air can be derived.

BRIEF DESCRIPTION OF THE DRAWINGS

These above and other objects will be readily apparent to persons of ordinary skill through the detailed description of the preferred embodiments below and the accompanying drawings in which.

DETAILED DESCRIPTION OF THE PREFERRED EMBODIMENT

Figure 1:
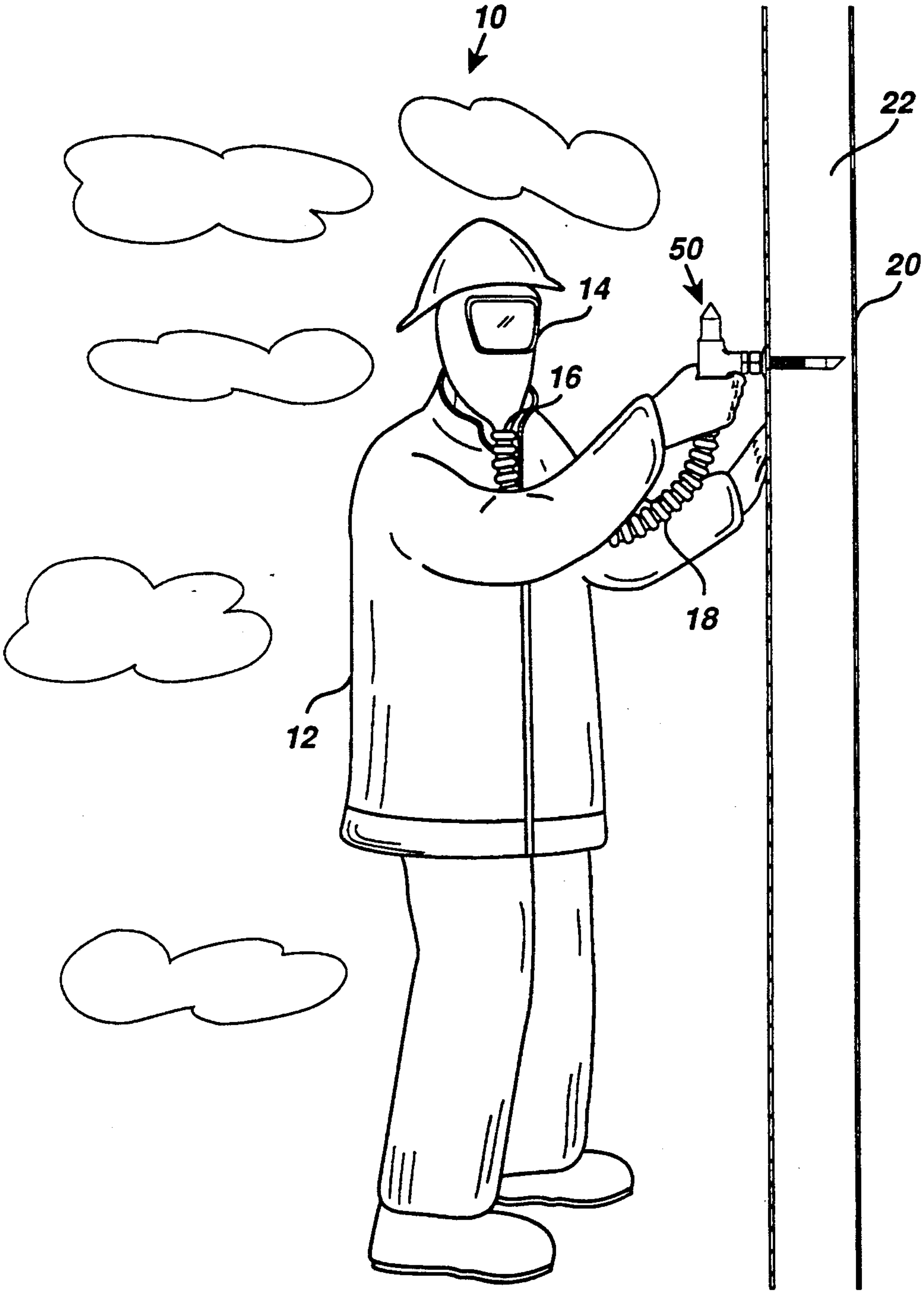
FIG. 1 is a diagram showing one application of the apparatus of the present invention.
Figure 2:
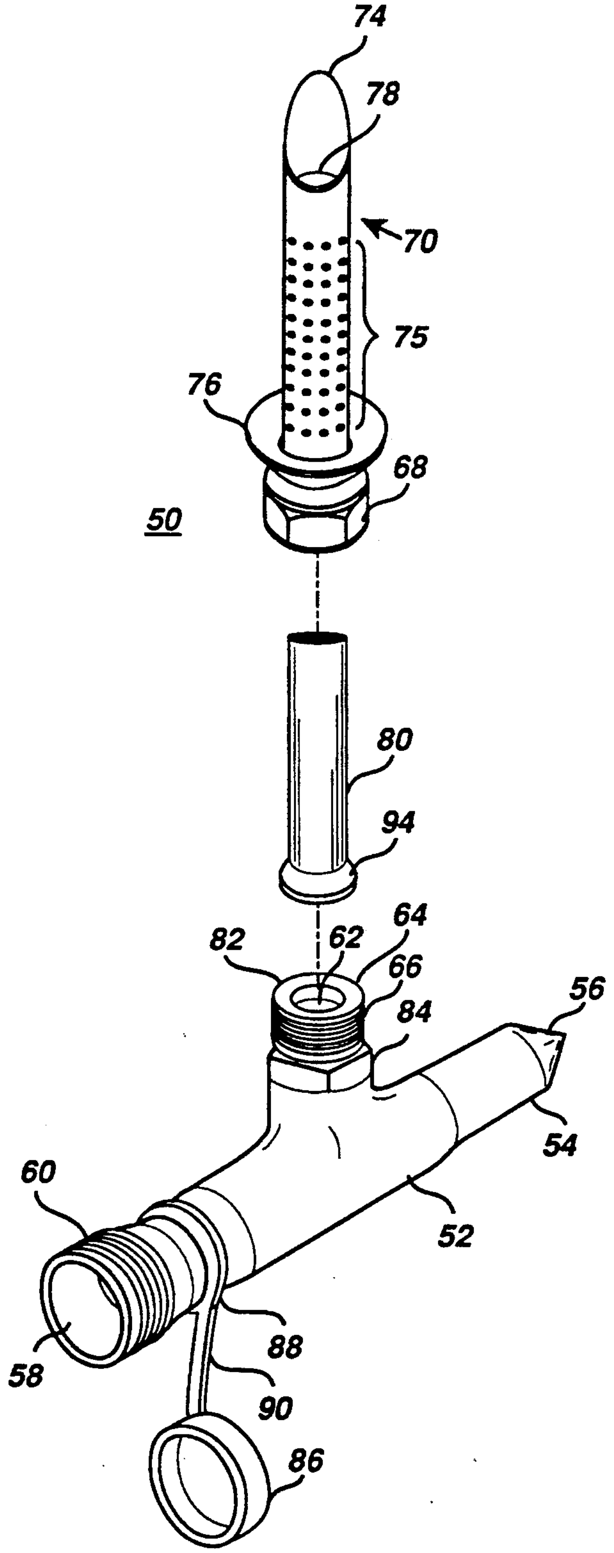
FIG. 2 is an exploded view in perspective of one embodiment of the breathing apparatus of the present invention.
Figure 3:
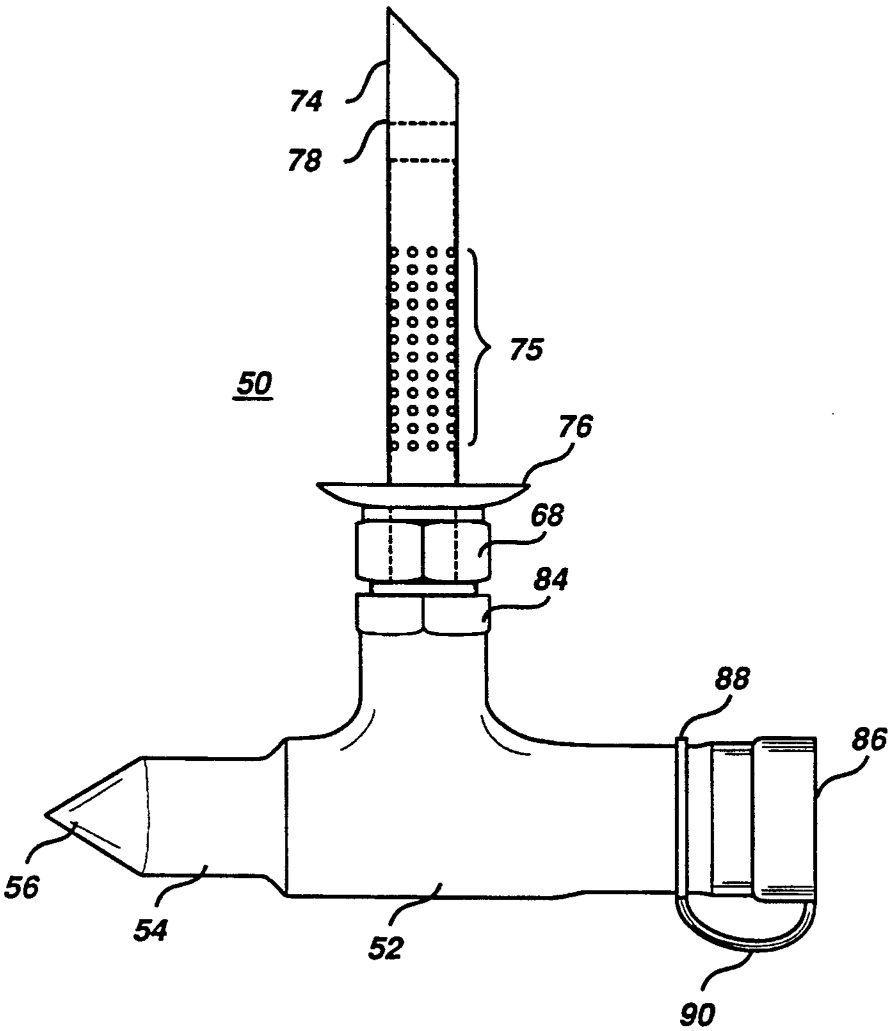
FIG. 3 is side view of one embodiment of the breathing apparatus of the present invention, showing the sealing end cap in a closed position.

The present invention provides a source of breathable air to firefighters and occupants of buildings in situations where ambient smoke created by fire has rendered atmospheric air unsuitable for breathing or in situations where a source of air, such as a tank of compressed air has been exhausted. Referring now to FIG. 1, typically, when a firefighter enters a burning structure 10, ambient air is unsuitable for breathing because of the large concentration of smoke and toxic fumes. Accordingly, in most situations, firefighters enter the burning structure 10 equipped with flame proof, heat resistent garments 12 as well as a protective face mask 14 which provides protection from heat and harmful gases. The protective face mask 14 typically includes an air inlet 16 which is coupled to an air line 18. The air line 18 is further coupled to a self contained breathing apparatus, which typically comprises one or more portable tanks of compressed air (not shown). In many cases, firefighters or occupants can be trapped in a burning structure for a sufficient time to exhaust the supply of air stored in the portable tanks. In prior systems, this situation has resulted in the suffocation or death of firefighters and occupants of the burning structure. However, the present invention provides a means of obtaining a source of breathable air even after the source of compressed air has been exhausted.

It is well known that in most modern structures, walls are constructed with hollow interior cavities as depicted by wall 20 having hollow interior cavity 22. In burning structures, the air contained in the hollow interior cavity of walls is typically not affected when the surrounding structure is burning, or is affected long after the ambient atmosphere is rendered unsuitable for breathing. This is primarily due to the fact that the internal cavity 22 of most walls is sealed by beams, studs and the associated wall covering material. If unsuitable air is encountered in a wall cavity, the apparatus 50 can be used to readily access a different wall cavity containing breathable air. According to the principles of the present invention, the interior cavity of a hollow wall may provide a sufficient supply of air to sustain one or more persons for a substantial period of time before accessing another cavity is required.

The apparatus 50 provides a means for accessing the air contained in the internal cavity of a wall. The air contained within a wall may be coupled through the apparatus 50 to the face mask 14 by air line 18.

Referring now to FIGS. 2–5B, the apparatus 50 provides a means for creating an opening in a wall and for coupling the air stored in the internal cavity of a wall to an outlet in the apparatus 50. The apparatus 50 includes a hollow body 52 which acts as a conduit for air flow. The hollow body 52 is preferably substantially cylindrical and is preferably formed of a rigid material, such as steel, high impact plastic or similar material. One end of hollow body 52 can be configured as a peen member 54. A rigid plastic body is preferred to reduce the likelihood of electrical shock from contact with electrical cables in the wall cavity 22. Alternatively, a steel embodiment can be covered by a plastic coating to prevent electrical conduction.

Peen member 54 is preferably formed of solid steel and includes a tapered tip 56 adapted for creating openings in walls. The other end of hollow body 52 can be provided with an outlet port 58. Outlet port 58 is preferably cylindrical and includes a threaded exterior portion 60 which is adapted to receive one end of an air line as shown in FIG. 1.

The apparatus 50 can further include an inlet port 62 disposed in the wall of hollow body 50 wherein the inlet port 62 is preferably configured with a cylindrical wall 64. The exterior of cylindrical wall 64 is configured with threads 66 adapted to receive a retaining nut 68 coupled to a piercing means 70.

Figures 5A, 5B:
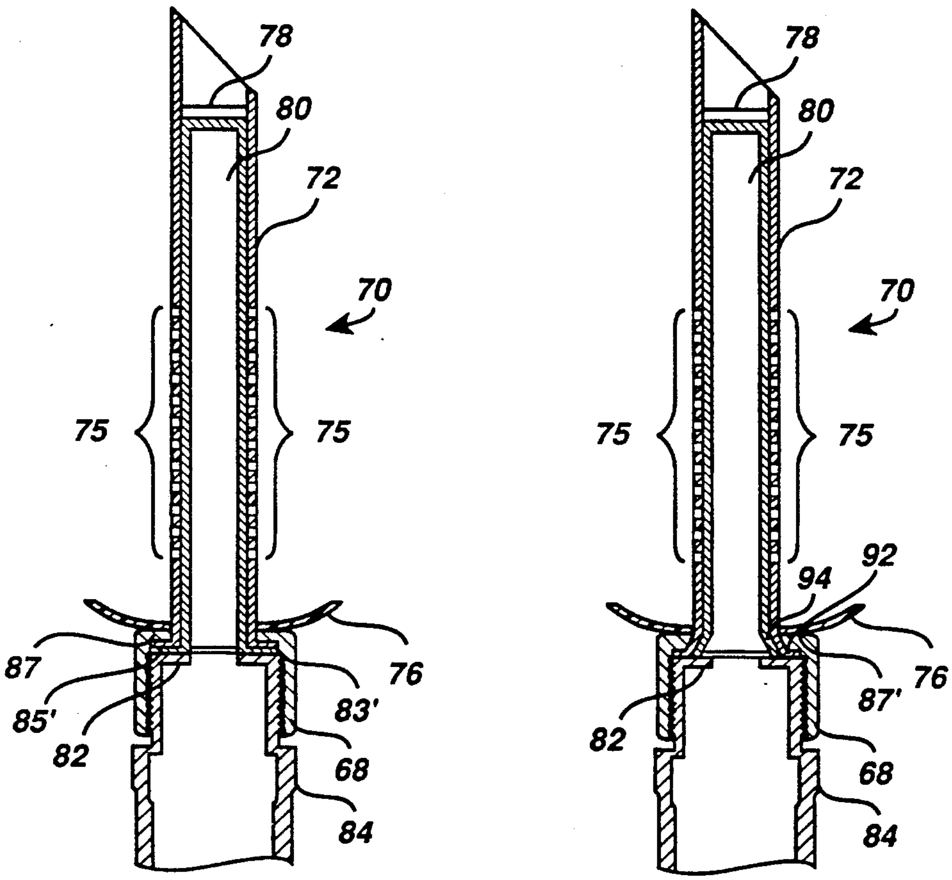
FIGS. 5A and 5B are cross-sectional views of alternate embodiments of means for securing a wall piercing means to the body of the apparatus.

Piercing means 70 preferably comprises a hollow shaft 72 having a beveled piercing edge 74 formed by a knife surface on the interior periphery of the distal end of the piercing means. A plurality of orifices 75 are disposed in the wall of hollow shaft 72. A concave annular seal member 76 is preferably disposed about the exterior of hollow shaft 72 abutting retaining nut 68. Annular seal 76 provides a means of sealing piercing means 72 in an aperture in a wall when apparatus 50 is in use. A baffle 78 is disposed at the distal end of hollow shaft 72, with respect to body 52, wherein baffle 78 prevents the entry of foreign material and air through the end of piercing means 70. The baffle 78 is preferably remote from the distal end of the piercing means to form a recess for collecting wall debris upon insertion the piercing means into the wall 20. A porous filter element 80 is preferably disposed internally, and coextensive within hollow shaft 72, to filter particulate matter entering orifices 75. Piercing means 70 can be integrally formed with hollow body 52 or can be a separate component coupled to hollow body 52. Piercing means 70 is preferably coupled to inlet port 62 with retaining nut 68 which engages the threaded cylindrical wall 66 of inlet port 62. Inlet port 62 preferably extends radially from the hollow body 52 and is configured with a hexagonal step portion 84 which is adapted to receive a wrench for tightening nut 68 when attaching piercing means 70 to hollow body 52. Inlet port 62 further includes an annular ledge 82 wherein porous filter element 80 is held in place by abutting annular ledge 82 when piercing means 72 is attached to inlet port 62. Specifically, hollow shaft 72 may be configured with a stepped annular flange 83. An annular flange 85 of filter element 80 engages the stepped portion of stepped annular flange 83. The annular stepped flange 83 and the annular flange 85 are tightly held in engagement with annular ledge 82 by the force provided by retaining nut 68 which is configured with an annular ledge 87 which opposes stepped annular flange 83. In addition, filter element 80 can be configured with an outside diameter which is slightly larger than the inside diameter of hollow shaft 72, thus providing a pressure fit engagement which holds filter element 80 in place when inserted in hollow shaft 72. Alternate means for assembling filter element 80 and piercing means 70 are shown in FIGS. 5A and 5B, respectively.

A sealing cap 86 may be attached to hollow body 52 with a retaining ring 88 and joining strap 90. The sealing cap 86 is adapted to seal outlet port 58 when apparatus 50 is not in use.

The apparatus 50 performs two basic functions: creating an aperture in a wall from which breathable air can be derived, and deriving the air from the wall after the aperture has been created. When fully assembled, the preferred apparatus 50 can be held in two basic manners. When attempting to create a perforation in a wall formed of concrete block or the like, the apparatus 50 may be held with the piercing means 70 functioning as a handle so that peen member 54 may be used as an impact device or chisel to create a desired opening in the concrete block. Once the opening or perforation has been created, or in cases wherein the wall is formed with a relatively soft material, such as plaster board, the apparatus 50 may be grasped about hollow body 52 wherein sufficient force may be applied to piercing means 70 to force piercing means 70 into the subject wall to a point wherein seal 76 engages the outer surface of the wall. Once apparatus 50 is installed in a wall, breathable air may be drawn from the internal cavity 22 of wall 20 through apertures 75 and filter 80. The air is then communicated through hollow shaft 72 and hollow body 52 which conduct the air from internal cavity 22 to outlet port 58 as indicated by arrows 89.

Figure 4:
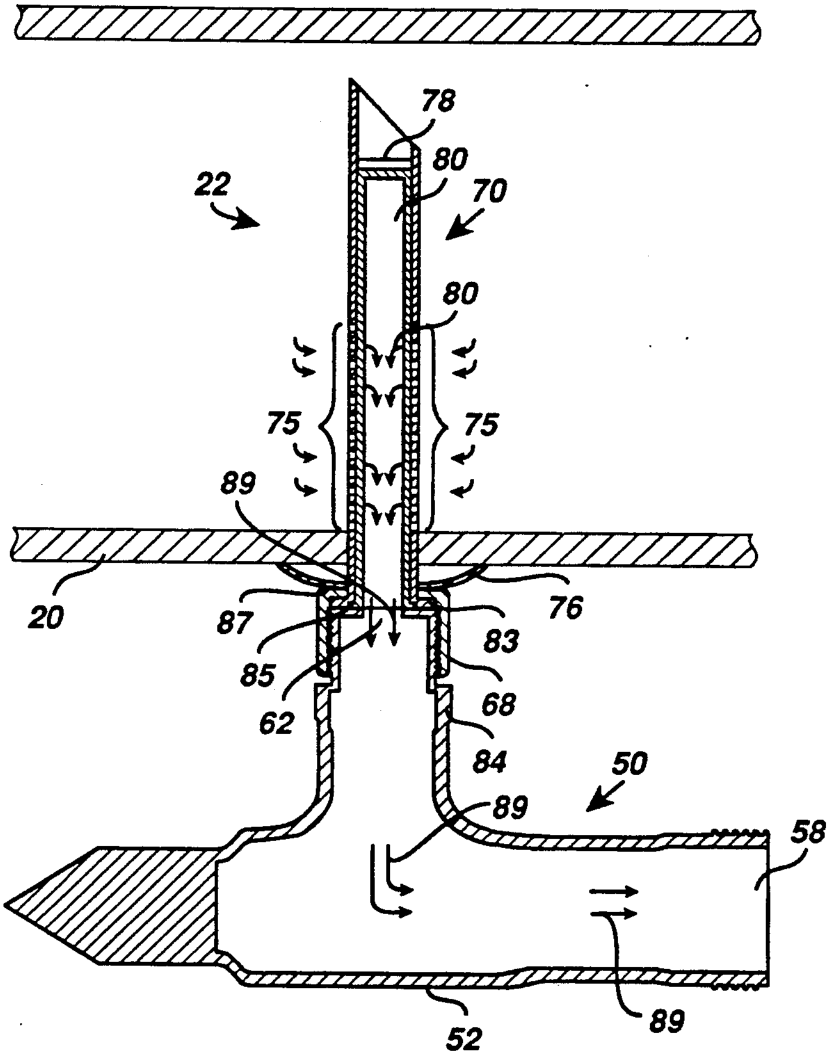
FIG. 4 is a cross-sectional view of one embodiment of the apparatus of the present invention.

As shown in FIG. 4, one principal function of the apparatus 50 is to provide an air conduit from the internal cavity 22 of a wall 20 the outlet port 58. When installed, piercing means 70 extends laterally into internal cavity 22 wherein air within internal cavity 22 flows through orifices 72 and filter element 80 into hollow body 52 as indicated by the flow arrows shown in FIG. 4. The air flowing into hollow body 52 is available for breathing through outlet port 58 which can be coupled to an air line (not shown). Air can also be derived by placing one's mouth directly over outlet port 58. The seal 76 restricts any contaminated air from entering the air stream represented by arrows 89.

Referring now to FIGS. 5A and 5B, alternate means for attaching piercing means 70 to inlet port 62 are shown. In the embodiment of FIG. 5A, hollow shaft 72 is configured with an annular flange 83' which abuts annular flange 85' of filter element 80. In this embodiment, both annular flange 83' and 85' are co-extensive with annular ledge 82 and can be held in tight engagement by the retaining force provided by opposing annular ledge 87 or retaining nut 68. In the alternative shown in FIG. 5B, hollow shaft 70 is configured with a flared annular flange 92 which engages a complementary flared annular flange 94 of filter element 80 wherein both flared annular flange 92 and flared annular flange 94 abut against annular ledge 82. A flared annular ledge 87' of retaining nut 68 secures the hollow shaft 72 and filter element 80 in concentric alignment with inlet port 62.

Figure 6:
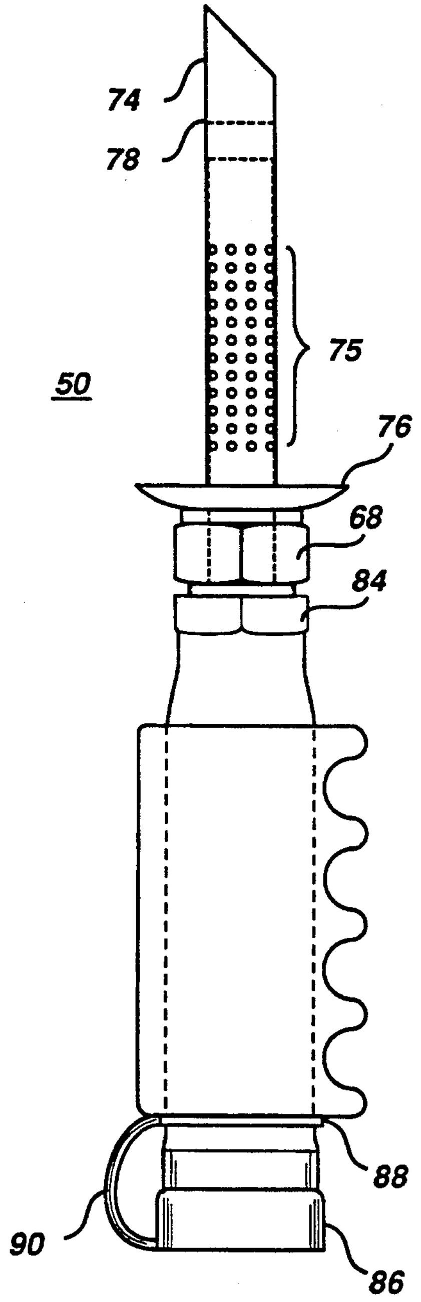
FIG. 6 is a side view of a second embodiment of the breathing apparatus of the present invention.

Referring now to FIG. 6, the invention can be embodied in an alternative apparatus 50 suitable for use by occupants of high-rise buildings and the like. Firefighters encounter smoke filled environments in residential, commercial and industrial building structure. In some instances, the only available wall cavity is surrounded by concrete block, particularly in industrial structures. Accordingly, an apparatus of the invention having a peen member for accessing the wall cavity through hard material, such as concrete block, is preferred. In contrast, the interior walls of many residential and office structures are made of relatively soft materials, such as plaster board or particle board, so that the need for a peen member in a t-shaped hammer configuration is reduced. Accordingly, a second preferred embodiment of the invention for use by occupants of high-rise buildings or similar structures can be constructed as an axial spike.

The spike 50 preferably comprises piercing means structure similar to that of the embodiments shown in FIGS. 1-5 B. The piercing means has orifices 75 for receiving air into the hollow interior of the piercing means. The air is filtered through a filter medium (not shown) and is conducted to the hollow interior of body member 52. The air can then be received from outlet port 58, which is shown as covered by protective cap 86 secured to body member 52 by retaining 88 and joining strap 90. The outlet port can be coupled to an air line and full face mask, as typically used by firefighters. Alternatively, a compact mouth-nose mask and airline can be used to breath air from the outlet port 58. Also, the air from outlet port 58 can be breathed directly by placing the user's mouth on outlet port 58.

The body member 52, which serves as a handle for holding and driving the spike 50 into a wall, can be provided with a grip 53. The entire spike can be manufactured of a rigid material, such as steel, plastic and the like. In the steel embodiment, the grip 53 can be made of an insulating material to prevent electrical shock from contact between the spike 50 and electrical cables in the cavity of the pierced wall.

The spike 50 preferably provides a rigid hilt 79 for limiting the penetration of the spike 50 into a pierced wall. A seal member, such as annular sealing ring 76, can be associated with the hilt 79 to sealing engage the spike 50 with the pierced wall to prevent the mixture of contaminated air with the breathable air flow into the spike 50.

Figure 7:
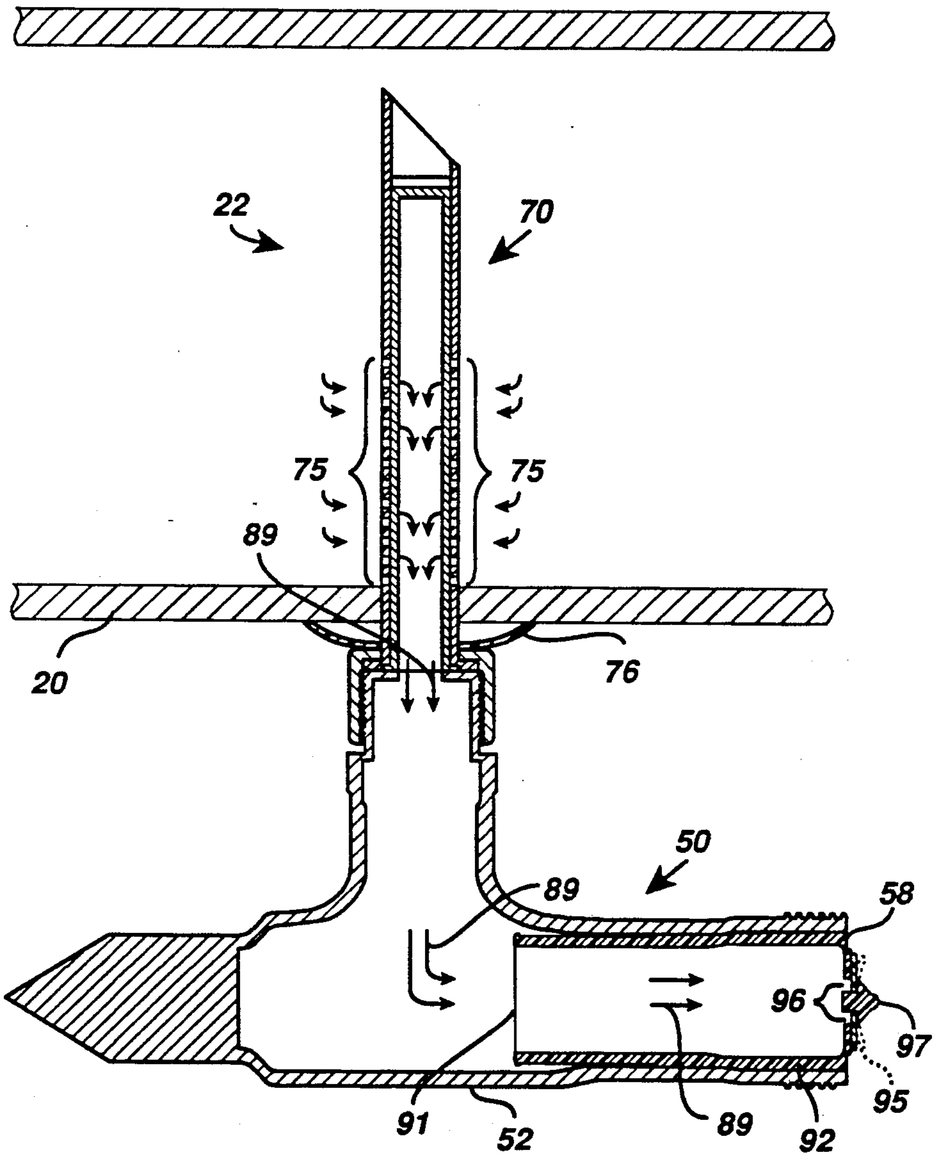
FIG. 7 is a cross-sectional view of an embodiment of the apparatus equipped with a one-way valve.

Referring to FIG. 7, the apparatus 50 preferably includes structure for preventing exhaled air, smoke and other toxins in the room from contaminating the source of breathable air in the wall cavity 22 through the apparatus 50. The apparatus 50 may be shared by two or more people or may be separated from an air mask temporarily, thereby providing a temporary passage for contaminated air or smoke through the hollow body 52 and piercing means 70 to the wall cavity 22. Additionally, exhaled air from a user may inadvertently be blown through the apparatus 50 to the source of breathable air.

The apparatus 50 therefore preferably provides valve means which allows passage of breathable air from wall cavity 22 through the apparatus 50 but restricts the flow of smoke or contaminated air and prevents the introduction of exhaled air to the wall cavity 22. Preferably, the valve means is a tubular flutter-valve assembly 91. The valve assembly 91 has a tubular body 92 which can be readily inserted in the hollow body 52 through the outlet 58 and secured by friction fit or other suitable means. The valve assembly 91 provides a flexible, rubber valve disc 95 which under back flow pressure seals valve ports 96, formed in the outlet end of the valve body 92, to prevent the flow of exhaled air into the hollow body 52 through the outlet 58. When a vacuum is drawn on outlet 58 by a user, the valve disc 95 resiliently bends about retaining post 97 to open valve ports 96 and permit passage of breathable air 89.

Figure 8:
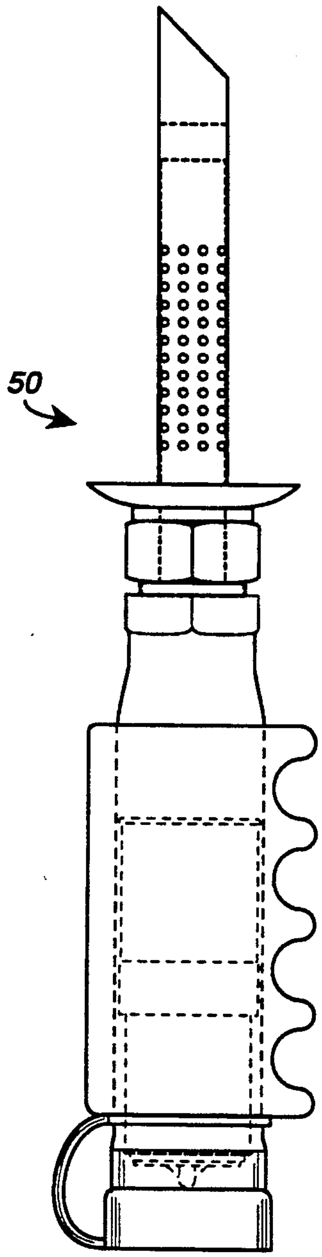
FIG. 8 is a side view of the second embodiment of the apparatus shown in FIG. 6, equipped with a one-way valve.

The valve means can be provided in other constructions, such as a caged ball valve assembly. Also, the valve means can be located at different positions in the apparatus 50. As shown in FIG. 8, the preferred flutter valve assembly 91 can also be disposed in the handle of the spike 50.

Figure 9:
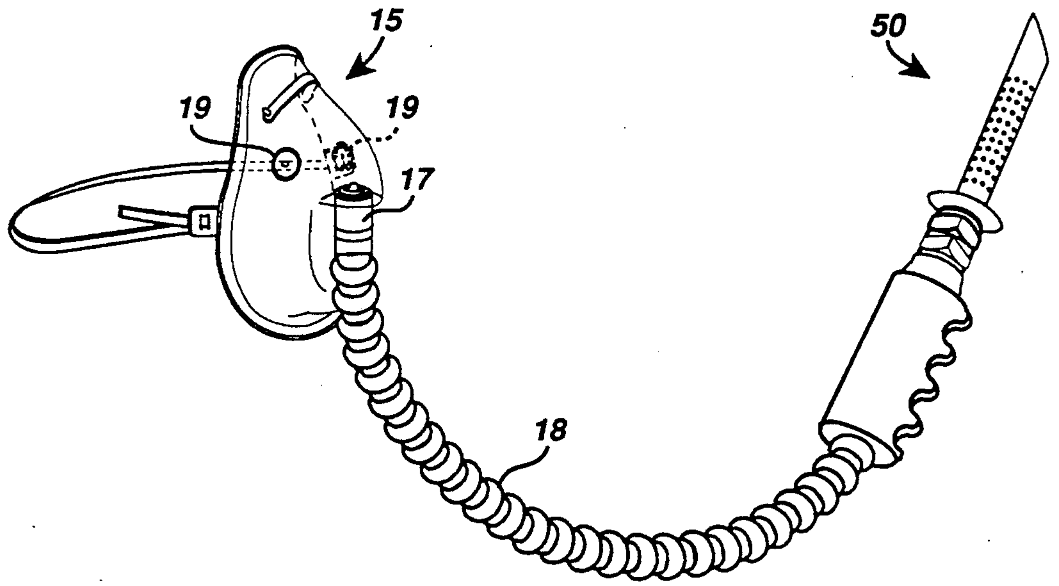
FIG. 9 is a perspective view of the apparatus of the invention in combination with a valved air mask.

Referring to FIG. 9, the valve means can alternatively or additionally be provided in an air mask 15 connected to the spike 50 by an air line 18. The air mask 15 includes an inlet valve assembly 17 which permits inhalation of air from apparatus 50 but prohibits exhaled air from entering air line 18 for passage to apparatus 50. The inlet valve assembly 17 can include a flutter-type valve, a ball valve or similar one-way air valve. The air mask 15 can also provide outlet valves 19 which include reciprocating rubber valve discs covering a series of apertures to permit the evacuation of exhaled air out of the mask 15 but prevent the introduction of smoke or other contaminants from the surrounding area into the mask 15.

The space between the surface of the piercing means and the surrounding hole in the wall can also provide passage for smoke to contaminate the wall cavity air source. Upon insertion into a wall, the wall material can break away, thereby forming a slightly larger aperture than the shaft of the apparatus. As discussed previously, the seal member 76 engages the wall surface surrounding the pierced hole to seal the passage thus formed.

Constant hand pressure should be exerted to maintain a reliable seal.

Figure 10:
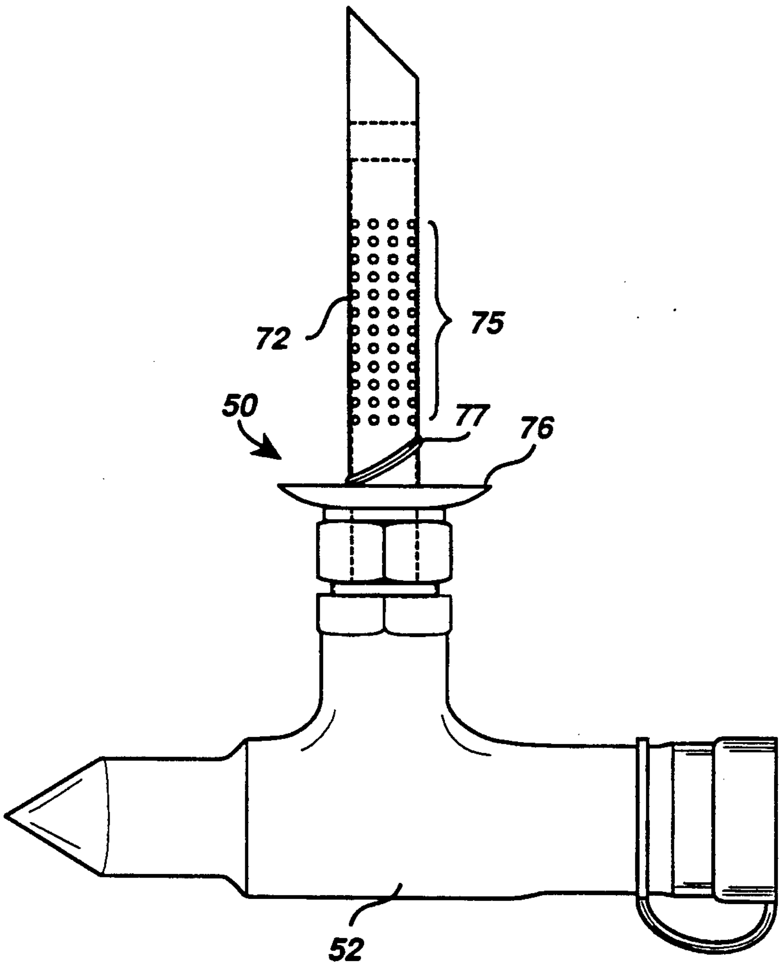
FIG. 10 is a side view of an embodiment of the invention wherein the piercing means is equipped with a locking thread.

Referring to FIG. 10, the apparatus 50 can also provide a locking thread 77 as an alternative to constant hand pressure for the sealing engagement of the piercing means with the associated, pierced wall. The locking thread 77 is preferably integrally formed on the shaft 72 proximate the hilt 76. The locking thread 77 can wrap about the shaft 72 from one quarter to one complete revolution and preferably wraps about one half revolution.

Thus, the user can grip the surrounding wall with the locking thread 77, and by rotating the body 52, bring the sealing member 76 into sealing contact with the wall so that contaminated air and smoke cannot pass through the gap formed between the wall aperture and the shaft 72. Further, the locking thread 77 enables the apparatus 50 to more securely engage the wall so that the user may release the apparatus 50 after insertion, thereby having use of his hands for other purposes.

In summary, an improved method and apparatus for providing a source of breathable air in a burning building has been described. Accordingly, other uses and modifications of the methods and apparatus of the present invention will be readily apparent to persons of ordinary skill in the art without departing from the principles present invention. All of such uses and modifications are intended to fall within the scope of the appended claims.

I claim:

1. A breathing apparatus for retrieving breathable air from a wall cavity in a burning building, said apparatus comprising:

a hollow body member;

a hollow piercing means operatively connected to said hollow body, said piercing means including a plurality of orifices for receiving air within the wall cavity into said hollow body, said hollow body providing an outlet port for allowing passage of air out of said hollow body to a user; and valve means operatively connected to said outlet port for allowing passage out of said hollow body but prohibiting back flow of smoke and air into said hollow body.

2. The apparatus of claim 1, wherein said valve means is disposed in said hollow body.

3. The apparatus of claim 1, wherein said valve means is a flutter-type valve.

4. The apparatus of claim 1, further comprising:

an air mask connected to said hollow body member and wherein said valve means is disposed in said air mask.

5. The apparatus according to claim 4, wherein the valve means is a flutter-type valve.

6. A breathing apparatus for retrieving breathable air from a wall cavity in a burning building, said apparatus comprising:

a hollow body member;

a hollow piercing means operatively connected to said hollow body, said piercing means including a plurality of orifices for receiving air within the wall cavity into said hollow body, said hollow body including an outlet port for allowing passage of air out of said hollow body; and locking means for securing said piercing means through material of a wall adjacent said wall cavity when said piercing means is inserted into the wall and said hollow body is rotated relative to the wall.

7. The apparatus according to claim 6, further comprising:

an annular sealing member disposed about said piercing means adjacent said hollow body, whereby said annular sealing member can be sealingly engaged against the wall when said locking thread is rotated into the wall.

* * * * *